(12) United States Patent
Sanso

(10) Patent No.: US 6,350,468 B1
(45) Date of Patent: Feb. 26, 2002

(54) DOUBLE CAPSULE FOR THE ADMINISTRATION OF ACTIVE PRINCIPLES IN MULTIPLE THERAPIES

(75) Inventor: Giovanni Sanso, Milan (IT)

(73) Assignee: Axcan Pharma Inc., Quebec (CA)

( * ) Notice: Subject to any disclaimer, the term of this patent is extended or adjusted under 35 U.S.C. 154(b) by 0 days.

(21) Appl. No.: 09/581,721

(22) PCT Filed: Dec. 14, 1998

(86) PCT No.: PCT/EP98/08167

§ 371 Date: Jun. 16, 2000

§ 102(e) Date: Jun. 16, 2000

(87) PCT Pub. No.: WO99/30693

PCT Pub. Date: Jun. 24, 1999

(30) Foreign Application Priority Data

Dec. 17, 1997 (IT) .......................... MI97A2788

(51) Int. Cl.⁷ .............................. A61K 9/64; A61K 9/48
(52) U.S. Cl. ................... 424/456; 424/451; 424/453; 424/454
(58) Field of Search ................. 424/451, 453, 424/454, 456, 460

(56) References Cited

U.S. PATENT DOCUMENTS

| | | | |
|---|---|---|---|
| 3,072,528 A | 1/1963 | Kludas et al. ............ | 167/55 |
| 4,606,909 A | 8/1986 | Bechguard et al. ........ | 424/21 |
| 4,627,808 A | 12/1986 | Hughes .................. | 425/270 |
| 4,642,233 A | 2/1987 | Urquhart et al. ......... | 424/19 |
| 4,695,466 A | 9/1987 | Morishita et al. ........ | 424/456 |
| 4,793,493 A | 12/1988 | Makiej, Jr. ............. | 206/538 |
| 4,822,619 A | 4/1989 | Eichel et al. ........... | 424/492 |
| 4,904,476 A | 2/1990 | Mehta et al. ............ | 424/456 |
| 4,936,461 A | 6/1990 | Makiej, Jr. ............. | 206/528 |
| 5,196,205 A | 3/1993 | Borody .................. | 424/653 |
| 5,256,684 A | 10/1993 | Marshall ................ | 514/398 |
| 5,310,555 A | 5/1994 | Zimmer .................. | 424/438 |
| 5,394,980 A | 3/1995 | Tsai .................... | 206/63.5 |
| 5,472,695 A | 12/1995 | Neeman et al. ........... | 424/195.1 |
| 5,501,857 A | 3/1996 | Zimmer .................. | 424/438 |
| 5,560,912 A | 10/1996 | Neeman et al. ........... | 424/195.1 |
| 5,582,837 A | 12/1996 | Shell ................... | 424/451 |
| 5,672,359 A | 9/1997 | Digenis et al. .......... | 424/463 |
| 5,674,858 A | * 10/1997 | McColm ................. | 514/154 |

FOREIGN PATENT DOCUMENTS

| | | | |
|---|---|---|---|
| DE | 27 29 068 | 1/1979 | ......... A61K/9/52 |
| FR | 1 454 013 | 8/1966 | |
| FR | 2 524 311 | 10/1983 | ......... A61K/9/54 |
| GB | 2 103 564 | 2/1983 | ......... A61K/9/48 |
| JP | 60193917 A | 10/1985 | ......... A61K/9/48 |
| WO | WO 8903219 | 4/1989 | ......... A61K/33/24 |
| WO | WO 89/03219 | * 4/1989 | |
| WO | WO 9211848 | 7/1992 | ......... A61K/31/29 |
| WO | WO 9602236 | 2/1996 | ......... A61K/9/20 |

* cited by examiner

Primary Examiner—Thurman K. Page
Assistant Examiner—Rachel M. Bennett
(74) Attorney, Agent, or Firm—Myers Bigel Sibley & Sajovec P.A.

(57) ABSTRACT

A pharmaceutical dosage form particularly suitable for the administration of active principles in multiple therapies is disclosed. The pharmaceutical dosage form is a double capsule where in an internal capsule is placed inside an external one. Each internal and external capsule includes one or more active principles. A double capsule according to the invention is preferably used in triple or quadruple therapies against the microorganisms Helicobacter Pylori. Advantages of this pharmaceutical dosage form consist in providing a simple posology for administration of two and more active principles, allowing the active principles to activate at the right intervals of time and in the preestablished quantities, and preventing interactions between active principles. In a preferred embodiment of the invention, the pharmaceutical dosage form has an external capsule containing bismuth subcitrate and metronidazole, and an internal capsule containing tetracycline and optionally omeprazole, which is used in therapy for eradication of *Helicobacter pylori*.

37 Claims, No Drawings

DOUBLE CAPSULE FOR THE ADMINISTRATION OF ACTIVE PRINCIPLES IN MULTIPLE THERAPIES

This Application is a 371 of PCT/EP98/08167 filed on Dec. 14, 1998.

FIELD OF THE INVENTION

This invention concerns a pharmaceutical dosage form consisting of a double capsule for the administration of active principles in multiple therapies. The double capsule consists in a capsule placed inside another one.

BACKGROUND OF THE INVENTION

Therapies for the administration of more than one active principle at a time or at short intervals of time are already well known. The most common pharmaceutical dosage form consists of tablets for the various active principles with coatings allowing the differentiated release of the chemical compounds.

Among said therapies, the most common ones are those concerning affections of the digestive system caused by the presence of the microorganisms Helicobacter Pylori, such as gastritis and gastroduodenal ulcers, which in due time can lead to tumoral forms. As known, *Helicobacter pylori* is a modern appellation of *Campilobacter pylori*.

U.S. Pat. No. 5,196,205 (corresponding to patent application WO 89/03219) describes a method for the treatment of those pathological agents, consisting of the administration of a compound of bismuth, an antibiotic belonging to the group of penicillins and tetracycline and a second antibiotic such as metronidazole. The relevant therapy consists of the administration of three tables (one for each active principle) several times a day.

Consequently, this therapy results in being extremely complicated. The therapy described by U.S. Pat. No. 5,196,205 has been further modified by the addition of a fourth active principle, omeprazole which reduces the gastric secretion by inhibiting irreversibly enzyme H+/K+ATP. Omeprazole must be administered at a different time from the above-mentioned active principles, which are determined by the physician according to the seriousness of the disease, the age of the patient and other factors which could affect its efficacy.

Therefore, it can certainly be stated that therapies requiring a complicated posology such as multiple therapies, are subject to mistakes that can compromise the outcome of the therapy itself.

Other patents and patent applications describing single or multiple therapies for eradication of Helicobacter pylori are known such as U.S. Pat. No. 5,472,695, U.S. Pat. No. 5,560,912, U.S. Pat. No. 5,582,837, WO 92/11848 and WO 96/02237. None of these previous patents and patent applications overcome the problem of the interaction between active principles by using a way as simple and ingenious than the one proposed by the present invention.

U.S. Pat. No. 5,310,555 and U.S. Pat. No. 5,501,857 teach to use double capsules for the delivery of nutritional supplements to animals.

Patent JP 60-193917 teaches a soft capsule containing several smaller soft capsules.

Patent DE 2,729,068 teaches a standard hard gelatine capsule having an additional hard gelatine capsule inside, with the same or different dissolution characteristics.

Patent FR 2,524,311 teaches a double capsule and a triple capsule.

Patent FR 1,454,013 teaches a double capsule where the inner capsule has retarded released characteristics.

Patent application GB 2,103,564 teaches a capsule assembly for oral administration of a prophylactic drug characterized by a frangible outer capsule and an inner edible capsule with an air-space therebetween allowing the user to bite through the outer capsule and swallow the inner capsule intact.

Among multiple therapies for eradication of *Helicobacter pylori*, the following combinations of active principles have been tested on humans, and published:

1. Amoxicilline, metronidazole and furazolidone;
2. Bi Subsalicylate, lansoprazole and clarithromycine;
3. Bi Subsalicylate, roxithromycine, metronidazole and ranitidine;
4. Clarithromycine, colloidal bismuth, subcitrate and furazoline;
5. Colloidal bismuth subcitrate, amoxicilline and metronidazole;
6. Ebrotidine, amoxicilline and metronidazole;
7. Lansoprazole, amoxicilline and azithromycine;
8. Lansoprazole, amoxicilline and clarithromycine;
9. Lansoprazole, amoxicilline and rebamipide;
10. Lansoprazole, clarithromycine and furazoline;
11. Lansoprazole, azithromycine and metronidazole;
12. Lansoprazole, miconazole and amoxicilline;
13. Lansoprazole and norfloxacine;
14. Metronidazole and dirithromycine;
15. Omeprazole, amoxicilline and azithromycine;
16. Omeprazole, amoxicilline, clarithromycine and metronidazole;
17. Omeprazole, amoxicilline, metronidazole and bismuth;
18. Omeprazole, amoxicilline and rebamipide;
19. Omeprazole, amoxicilline and tinidazole;
20. Omeprazole and amoxicilline;
21. Omeprazole and azithromycine;
22. Omeprazole, bismuth and ciprofloxacine;
23. Omeprazole, bismuth and clarithromycine;
24. Omeprazole, clarithromycine and tinidazole;
25. Omeprazole and dirithromycine;
26. Omeprazole, lansoprazole and rebamipide;
27. Omeprazole, metronidazole and amoxicilline;
28. Omeprazole, metronidazole and azithromycine;
29. Omeprazole, metronidazole and clarithromycine;
30. Omeprazole and norfloxacine;
31. Omeprazole, sucralfate, metronidazole and tetracycline;
32. Omeprazole, clarithromycine and tinidazole;
33. Pantoprazole, clarithromycine and amoxicilline;
34. Pantoprazole and clarithromycine;
35. Ranitidine bismuth citrate, clarithromycine and tetracycline;
36. Ranitidine bismuth citrate and clarithromycine;
37. Ranitidine bismuth citrate, metronidazole and clarithromycine;
38. Ranitidine bismuth citrate and cefuroxime;
39. Rifaximin and erythromycine;
40. Omeprazole, bismuth, tretracycline and metronidazole;
41. Omeprazole, bismuth subcitrate, tretracycline and metronidazole;
42. Bismuth subcitrate, tretracycline and metronidazole.

SUMMARY OF THE INVENTION

An object of the present invention is the use of a pharmaceutical dosage form comprising two capsules one placed inside the other for the administration of active principles in multiple therapies, in the therapy against the microorganisms *Helicobacter pylori*.

In accordance with the present invention, that object is achieved with the use of a soluble salt of bismuth, a first antibiotic and a second antibiotic for the preparation of a pharmaceutical dosage form comprising two capsules one placed inside the other for a triple therapy against the microorganisms *Helicobacter pylori*, wherein the external capsule comprises the soluble salt of bismuth and the first antibiotic, and the internal capsule comprises the second antibiotic.

The object of the present invention is also achieved with the use of a soluble salt of bismuth, a first antibiotic, a second antibiotic, and a $K^+/Na^+$ATPase inhibitor or anti-$H_2$, for the preparation of a pharmaceutical dosage form comprising two capsules one placed inside the other for a quadruple therapy against the microorganisms Helicobacter pylori, wherein the external capsule comprises the soluble salt of bismuth and the first antibiotic, and the internal capsule comprises the second antibiotic and the $K^+/Na^+$ ATPase inhibitor or anti-$H_2$.

The object of the present invention is further achieved with the use of a soluble salt of bismuth, a first antibiotic, a second antibiotic, and a $K^+/Na^+$ATPase inhibitor or anti-$H_2$, for the preparation of a pharmaceutical dosage form comprising two capsules one placed inside the other for a quadruple therapy against the microorganisms Helicobacter pylori, wherein the external capsule comprises the soluble salt of bismuth, the first antibiotic, and the $K^+/Na^+$ATPase inhibitor or anti-$H_2$, and the internal capsule comprises the second antibiotic.

The object of the present invention is also further achieved with the use of a soluble salt of bismuth, a first antibiotic, a second antibiotic, and a $K^+/Na^+$ATPase inhibitor or anti-$H_2$, for the preparation of a first pharmaceutical dosage form and a second pharmaceutical dosage form, the first pharmaceutical dosage form comprising two capsules one placed inside the other for a quadruple therapy against the microorganisms Helicobacter pylori, wherein the external capsule comprises the soluble salt of bismuth and the first antibiotic, and the internal capsule comprises the second antibiotic; the second pharmaceutical dosage form comprising a $K^+/Na^+$ATPase inhibitor or anti-$H_2$.

An advantage of the pharmaceutical dosage form of the invention is to be used in multiple therapies, which allows a simple and safe posology.

One of the major advantages of the pharmaceutical dosage form of the present invention is that it overcomes problems related with the interaction of the active principles by means of a physical barrier.

The characteristics and advantages of the invention will be better understood after reading the following non restrictive description.

DETAILED DESCRIPTION OF THE INVENTION

Double Capsule

The present invention provides a pharmaceutical dosage form for the administration of active principles in multiple therapies featured by the presence of two capsules one placed inside the other and including respectively one or more active principles. This pharmaceutical dosage form is called double capsule and the two capsules are respectively called internal capsule and external capsule.

Both internal and external capsules are preferably made of hard gelatin. If desired, the internal capsule may be made of gelatin treated so as make it gastro-resistant or slow release.

The capsules already on the market are identified by numbers or letters according to their size (length, diameter and thickness), as indicated in Table 1 (CAPSUGEL MULTISTATE FILE, 2° Ed.)

TABLE 1

SIZE OF THE JELLY CAPSULES

| Type of capsule | Format of Capsule | Total length of the capsule (nm +/− 0.3 nm) | Diameter of the external body (nm) | Thickness of the wall (nm) |
|---|---|---|---|---|
| CONI-SNAP SNAP-FIT | 000 | 26.14 | 9.55 | |
| | 00 | 23.3 | 8.18 | 0.231 |
| | 0+ | 23.8 | 7.36 | 0.224 |
| | 0 | 21.2 | 7.33 | 0.212 |
| | 1 | 19.0 | 6.63 | 0.216 |
| | 2 | 17.5 | 6.07 | 0.211 |
| | 3 | 15.6 | 5.57 | 0.203 |
| | 4 | 13.9 | 5.05 | 0.198 |
| | 5 | 11.0 | 4.64 | 0.173 |
| CONI-SNAP SUPRO | A | 18.00 | 8.18 | 0.231 |
| | B | 14.20 | 8.18 | 0.231 |
| | C | 13.50 | 7.33 | 0.224 |
| | D | 12.60 | 6.63 | 0.216 |
| | E | 11.60 | 6.07 | 0.211 |
| LICAPS | 0 | 21.70 | 7.33 | 0.224 |
| | 1 | 19.70 | 6.63 | 0.216 |
| | 2 | 17.90 | 6.70 | 0.211 |

Accordingly to the invention, the double capsule has an internal capsule smaller than the external one, since according to this principle all the combinations of the Table 1 are possible except for the combination of external capsule of format 0+ with internal capsule of format A or O of any types of capsules. Such combinations are chosen to facilitate the use for the patient and according to the quantity of substance to be introduced into the two capsules. As a matter of fact, the volume between the two capsules and the volume of the internal capsule should be suitable to allow the insertion of the quantities foreseen by the therapeutic dosage. The internal capsule should preferably be a 2 or 3 format, while the external capsule should be respectively a 0+ or 1 format. In accordance with a preferred embodiment of the invention, an internal capsule of format 3 is inserted in an external capsule of format 0+.

Said pharmaceutical form is realised by means of an intermittent or continuous motion capsule filling machine equipped with dosators to feed empty capsules with powders, tablets, pellets or filled capsules. Examples of said capsule filling machines are the Zanazi 40 of the company IMA in Bologna and the model MG Futura level 02 of the company MG2 in Bologna. As an alternative, the new double capsule can be realised by means of a manual machine type Zuma 150 or 300 and type Parka-Davis/Capsugel.

Besides, it must be taken into consideration that even the movement of the capsules caused by the capsule filling machines, either automatic or manual, and the simple act of inserting the internal capsule are enough to form between the two capsules a layer of powder which keeps them separated.

Triple Therapy

This pharmaceutical dosage form is particularly suitable to be used in a triple therapy for the eradication of the pathologic agents Helicobacter pylori (also known as *Campilobacter pylori*), consisting of the administration of three active principles which are a soluble salt of bismuth, a first antibiotic and a second antibiotic. Each internal and external capsule contains one or more active principles.

The bismuth salt is preferably selected from the group consisting of bismuth subcitrate, bismuth aluminate, bismuth carbonate, bismuth citrate, colloidal bismuth subnitrate, bismuth germanate, bismuth germanium oxide, bismuth nitrate, bismuth oxide, bismuth oxychloride, bismuth phosphate, bismuth salicylate, bismuth subcarbonate, bismuth subnitrate, bismuth subsalicylate, bismuth tribromophenate, bismuth trioxide, bismuth vanadate, and bismuth vanadium tetraoxide. Bismuth salts may be used in a complex form. For example, bismuth biscalcitrate is a complex form of bismuth subcitrate.

The first antibiotic is selected from the group consisting of the nitroimidazoles. The nitroimidazoles are preferably selected from the group consisting of metronidazole, apronidazole, azomycine, benzonidazole, carnidazole, demetridazole, etanidazole, flunidazole, inisonidazole, nimorazole, ornidazole, panidazole, ronidazole, and tinidazole. Preferably, the first antibiotic is metronidazole.

The second antibiotic is selected from the group consisting of the macrolides and the compounds of the family of tetracyclines. The macrolides are preferably selected from the group consisting of azithromycine, clarithromycine and erythromycine. The compounds of the family of tetracyclines are preferably selected from group consisting of tetracycline, chlortetracycline, doxycycline, glycocycline, guamecycline, lymecycline, methacycline and sancycline. As known in the field, tetracycline correspond to tetracycline hydrochloride.

In accordance with a preferred embodiment of the invention, the external capsule contains bismuth subcitrate and metronidazole, and the internal capsule contains tetracycline.

When the external capsule, preferably containing bismuth subcitrate in a complex form and metronidazole, dissolves, it allows the complex bismuth to form a curative gel at the gastric level. After a certain period of time, according to the therapeutic indications, the internal capsule dissolves and releases tetracycline, which also acts at the gastric level.

The triple therapy as described above, usually consists of the administration of two identical double capsules several times a day, with no particular care as to the sequence of consumption and of the manipulation of the said double capsules. Ingestion of capsules is preferably done before meals and before a snack at bedtime.

Quadruple Therapy

An further way of realisation of the invention consists of the administration of a fourth active principle such as a $K^+/Na^+ATP$-ase inhibitor or a anti-$H_2$, together with the double capsule described above. In this case, the double capsule as foreseen by the invention will be destined to use in a quadruple therapy for the affections of the digestive system. $K^+/Na^+ATP$-ase inhibitor or anti-$H_2$ is selected from group consisting of BY841; cimetidine; ebrotidine; etintidine; famotidine; flunarizine; ICI-162,846; lansoprazole; metiamide; mifentidine; niperotidine; nizatidine; omeprazole; oxmetidine; pantoprazole; rabeprazole; ramixotidine; ranitidine; ritanserin; roxatidine acetate hydrochloride; ZKF-93479; SKF-94482; sufotidine; tiotidine; TY-11345; Wy-45,727; and zaltidine. Preferably, omeprazole is used as $K^+/Na^+ATP$-ase inhibitor.

The $K^+/Na^+ATP$-ase inhibitor or anti-$H_2$ may be introduced in the external capsule, in the internal capsule or in a separate pharmaceutical form. Since it is a requirement that $K^+/Na^+ATP$-ase inhibitor or anti-$H_2$ reach the small intestine, it may be delivered embedded in the gastroresistant coated pellets, multiple small tablets or single tablet. Considering that $K^+/Na^+ATP$-ase inhibitor or anti-$H_2$ must be administered according to criteria other than those foreseen for triple therapy, double capsules without $K^+/Na^+ATP$-ase inhibitor or anti-$H_2$ may be alteratively administered to double capsules containing $K^+/Na^+ATP$-ase inhibitors or anti-$H_2$, following a therapeutic scheme prescribed by the physician, depending on the seriousness of the disease and the condition of the patient.

In accordance with another preferred embodiment of the invention, the external capsule contains bismuth subcitrate and metronidazole, and the internal capsule contains tetracycline and omeprazole.

Characteristics of the Invention

Preferably, both capsules contain excipients. These excipients are selected from the group consisting of magnesium stearate; talc; cellulose and its derivatives; silica and its derivatives; sugars; polyethylene-glycols; wax; mono, di- and tri-glycerides of hydrogenated fat acids; alcohols and acids at high molecular weight; and relevant mixtures thereof.

Both internal and external capsule containing the active principles as described above are stable at a temperature comprised between 5 and 50° C. and at a humidity comprised between 35 and 65%.

Scope of the Invention

Preferred embodiments of the invention have been described above for triple therapy and quadruple therapy for the eradication of *Helicobacter pylori*. Although these embodiments are preferred for such therapies, it should be understood that the double capsule may contain other active principles in accordance with the invention. Thus, the combinations of active principles listed above in the background of the invention, may be used in the claimed pharmaceutical dosage form without departing from the scope of the claimed invention. For example, using the above listed combination no. 34, a double capsule having an external capsule containing clarithromycine and an internal gastroresistant capsule containing pantoprazole would fall within the scope of the claimed invention.

The following are stabilisation and dissolution trials together with an example for the realisation of the double capsule as foreseen by the invention, for explanatory and not limitative purposes.

Stability Trials

Two products have been analysed, respectively a single capsule containing coated tetracycline hydrochloride, bismuth biscalcitrate, metronidazole and a double capsule as foreseen by the invention containing, in the internal capsule, non-coated tetracycline and, in the external capsule, bismuth biscalcitrate and metronidazole.

A sample for each product to be analysed has been incubated at room temperature; 37° C. and 44° C. for a period of 1 month. At the time zero and at the end of the incubation period (1 month), an analysis of the macroscopic characteristics of the products under analysis has been performed.

Time Zero

Single capsule
External capsule: white
Content: mixture of white powder (bismuth biscalcitrate) and yellow powder (tetracycline hydrochloride)

Double capsule
External capsule: white
Internal capsule: brown
Content of the External capsule: white powder (bismuth biscalcitrate, metronidazole)
Content of the internal capsule: yellow powder (tetracycline hydrochloride)

TABLE 2

|  | AFTER 1 MONTH | | |
|---|---|---|---|
|  | ROOM TEMPERATURE | 37° C. | 44° C. |
| SINGLE CAPSULE | | | |
| External capsule | Slightly yellowish | White | white |
| Content | Mixture of white and yellow powder | Mixture of white and beige powder | Mixture of white and beige powder |
| DOUBLE CAPSULE | | | |
| External capsule | white | white | white |
| Internal capsule | brown | Brown | brown |
| Content of the External capsule | white powder | white powder | white powder |
| Content of the Internal capsule | yellow powder | yellow powder | yellow powder |

As it can be observed in Table 2, at the temperature 37° C. and 44° C., the content of the single coated capsule forms a beige-coloured product while the double capsule as foreseen by the invention does not form any degradation product. This effect is encouraged by the physical barrier represented by the coating of the internal capsule which does not allow the overflow of tetracycline.

Dissolution Trials

Five double capsules have been taken from one of the batches under examination, all five of them featured by the same characteristics:

| External capsule of format containing | 0+ |
|---|---|
| bismuth biscalcitrate | 215 mg |
| metronldazole | 125 mg |
| Internal capsule of format containing | 3 |
| tetracycline hydrochloride | 125 mg |

The capsules have been analysed separately and under identical conditions according to the criteria of the Pharmacopoeia of the United States USP 23 Ed. for the dissolution trial.

The purpose of the trial is to check if the exact quantity of tetracycline hydrochloride contained in the internal capsules dissolves (as indicated in the above Pharmacopoeia, which complies with all the other Pharmacopoeias). In this case, the presence of the external capsule and of its components should not affect the quantity of material under dissolution nor the time taken to release the active principle tetracycline hydrochloride.

The quantity of material to be dissolved within 60 minutes must not be inferior to 80% of the quantity present in the capsule according to said limit, foreseen by the Pharmacopoeia.

As for the double capsules, the following percentage dissolution results have been obtained:

Minimum value of dissolution 81.4%
Maximum value of dissolution 107.9%
Average value 100.0%
RSD ~9.7% (RSD=Relative Standard Deviation)

From the results obtained, it is clear that the double capsule as described by the invention is in compliance with the foreseen dissolution characteristics.

EXAMPLE 1

Capsules of format 3 have been prepared with the following content:

| Tetracycline hydrochloride | 125 mg |
|---|---|
| Gastroprotected omeprazole | 5 mg |
| Magnesium stearate | 5 mg |
| Talc | 5 mg |

Capsules of format 0+ have been prepared with the following content:

| Bismuth biscalcitrate | 215 mg (corresponding to 53,7 mg of Bismuth) |
|---|---|
| Metronidazole | 125 mg |
| Magnesium rate | 5 mg |
| Talc | 5 mg |

The capsules 0+ have not been completely sealed, so that it will be possible to open them again with a manual machine (Zuma), and insert in the inside the capsule of format 3, previously prepared.

The capsules have then been sealed and subjected to the controls concerning the disaggregation time, the average weight of the content, the sealing procedure, the assay of the single components and the microbiological purity, as foreseen in the Pharmacopoeia.

Although preferred embodiments of the invention have been described in detail herein, it is to be understood that the invention is not limited to the precise embodiments and that various changes and modifications may be effected therein without departing from the scope or the spirit of the invention.

What is claimed is:

1. Method for carrying out a triple therapy against the microorganisms *Helicobacter pylori* in a mammal comprising the oral administration to said mammal of a pharmaceutical dosage form comprising an internal capsule placed inside an external capsule, wherein the external capsule comprises a soluble salt of bismuth and a first antibiotic, and the internal capsule comprises a second antibiotic.

2. Method as claimed in claim 1, wherein the internal capsule further comprises a $K^+/Na^+$ATPase inhibitor or anti-$H_2$, whereby a quadruple therapy is carried out.

3. Method as claimed in claim 1, wherein the external capsule further comprises a $K^+/Na^+$ATPase inhibitor or anti-$H_2$, whereby a quadruple therapy is carried out.

4. Method as claimed in claim 1, further comprising the administration of a second pharmaceutical dosage form comprising a $K^+/Na^+$ATPase inhibitor or anti-$H_2$, whereby a quadruple therapy is carried out.

5. Method as claimed in claim 1, wherein:
the salt of bismuth is selected from the group consisting of bismuth subcitrate, bismuth aluminate, bismuth carbonate, bismuth citrate, colloidal bismuth subnitrate, bismuth germanate, bismuth germanium oxide, bismuth nitrate, bismuth oxide, bismuth oxychloride, bismuth phosphate, bismuth salicylate, bismuth subcarbonate, bismuth subnitrate, bismuth subsalicylate, bismuth tribromophenate, bismuth trioxyde, bismuth vanadate, and bismuth vanadium tetraoxide;

the first antibiotic is selected from the group consisting of the nitroimidazoles; and the second antibiotic is selected from the group consisting of the macrolides and the compounds of the family of tetracyclines.

6. Method as claimed in claim 5, wherein:

the nitroimidazoles are selected from the group consisting of metronidazole, apronidazole, azomycine, benzonidazole, carnidazole, demetridazole, etanidazole, flunidazole, misonidazole, nimorazole, ornidazole, panidazole, ronidazole, and tinidazole;

the macrolides are selected from the group consisting of azithromycine, clarithromycine and erythromycine; and the compounds of the family of tetracyclines are selected from the group consisting of tetracycline, chlortetracycline, doxycycline, glycocycline, guamecycline, lymecycline, methacycline and sancycline.

7. Method as claimed in claim 6, wherein:

the salt of bismuth is bismuth subcitrate;

the first antibiotic is metronidazole; and the second antibiotic is tetracycline.

8. Method as claimed in claim 2, wherein:

the salt of bismuth is selected from the group consisting of bismuth subcitrate, bismuth aluminate, bismuth carbonate, bismuth citrate, colloidal bismuth subnitrate, bismuth germanate, bismuth germanium oxide, bismuth nitrate, bismuth oxide, bismuth oxychloride, bismuth phosphate, bismuth salicylate, bismuth subcarbonate, bismuth subnitrate, bismuth subsalicylate, bismuth tribromophenate, bismuth trioxyde, bismuth vanadate, and bismuth vanadium tetraoxide;

the first antibiotic is selected from the group consisting of the nitroimidazoles;

the second antibiotic is selected from the group consisting of the macrolides and the compounds of the family of tetracyclines; and the $K^+/Na^+$ATPase inhibitor or anti-$H_2$ is selected from the group consisting of BY841; cimetidine; ebrotidine; etintidine; famotidine; flunarizine; ICI-162,846; lansoprazole; metiamide; mifentidine; niperotidine; nizatidine; omeprazole; oxmetidine; pantoprazole; rabeprazole; ramixotidine; ranitidine; ritanserin; roxatidine acetate hydrochloride; ZKF-93479; SKF-94482; sufotidine; tiotidine; TY-11345; Wy-45,727; and zaltidine.

9. Method as claimed in claim 8, wherein:

the nitroimidazoles are selected from the group consisting of metronidazole, apronidazole, azomycine, benzonidazole, carnidazole, demetridazole, etanidazole, flunidazole, misonidazole, nimorazole, ornidazole, panidazole, ronidazole, and tinidazole;

the macrolides are selected from the group consisting of azithromycine, clarithromycine and erythromycine; and the compounds of the family of tetracyclines are selected from the group consisting of tetracycline, chlortetracycline, doxycycline, glycocycline, guamecycline, lymecycline, methacycline and sancycline.

10. Method as claimed in claim 9, wherein:

the salt of bismuth is bismuth subcitrate;

the first antibiotic is metronidazole;

the second antibiotic is tetracycline; and the $K^+/Na^+$ATPase inhibitor or anti-$H_2$ is omeprazole.

11. Method as claimed in claim 1, wherein:

the salt of bismuth is selected from the group consisting of bismuth subcitrate, bismuth aluminate, bismuth carbonate, bismuth citrate, colloidal bismuth subnitrate, bismuth germanate, bismuth germanium oxide, bismuth nitrate, bismuth oxide, bismuth oxychloride, bismuth phosphate, bismuth salicylate, bismuth subcarbonate, bismuth subnitrate, bismuth subsalicylate, bismuth tribromophenate, bismuth trioxyde, bismuth vanadate, and bismuth vanadium tetraoxide;

the first antibiotic is selected from the group consisting of the nitroimidazoles;

the second antibiotic is selected from the group consisting of the macrolides and the compounds of the family of tetracyclines; and the $K^+/Na^+$ATPase inhibitor or anti-$H_2$ is selected from the group consisting of BY841; cimetidine; ebrotidine; etintidine; famotidine; flunarizine; ICI-162,846; lansoprazole; metiamide; mifentidine; niperotidine; nizatidine; omeprazole; oxmetidine; pantoprazole; rabeprazole; ramixotidine; ranitidine; ritanserin; roxatidine acetate hydrochloride; ZKF-93479; SKF-94482; sufotidine; tiotidine; TY-11345; Wy-45,727; and zaltidine.

12. Method as claimed in claim 11, wherein:

the nitroimidazoles are selected from the group consisting of metronidazole, apronidazole, azomycine, benzonidazole, carnidazole, demetridazole, etanidazole, flunidazole, misonidazole, nimorazole, ornidazole, panidazole, ronidazole, and tinidazole;

the macrolides are selected from the group consisting of azithromycine, clarithromycine and erythromycine; and the compounds of the family of tetracyclines are selected from the group consisting of tetracycline, chlortetracycline, doxycycline, glycocycline, guamecycline, lymecycline, methacycline and sancycline.

13. Method as claimed in claim 12, wherein:

the salt of bismuth is bismuth subcitrate;

the first antibiotic is metronidazole;

the second antibiotic is tetracycline; and the $K^+/Na^+$ATPase inhibitor or anti-$H_2$ is omeprazole.

14. Method as claimed in claim 4, wherein:

the salt of bismuth is selected from the group consisting of bismuth subcitrate, bismuth aluminate, bismuth carbonate, bismuth citrate, colloidal bismuth subnitrate, bismuth germanate, bismuth germanium oxide, bismuth nitrate, bismuth oxide, bismuth oxychloride, bismuth phosphate, bismuth salicylate, bismuth subcarbonate, bismuth subnitrate, bismuth subsalicylate, bismuth tribromophenate, bismuth trioxyde, bismuth vanadate, and bismuth vanadium tetraoxide;

the first antibiotic is selected from the group consisting of the nitroimidazoles;

the second antibiotic is selected from the group consisting of the macrolides and the compounds of the family of tetracyclines; and the $K^+/Na^+$ATPase inhibitor or anti-$H_2$ is selected from the group consisting of BY841; cimetidine; ebrotidine; etintidine; famotidine; flunarizine; ICI-162,846; lansoprazole; metiamide; mifentidine; niperotidine; nizatidine; omeprazole; oxmetidine; pantoprazole; rabeprazole; ramixotidine; ranitidine; ritanserin; roxatidine acetate hydrochloride; ZKF-93479; SKF-94482; sufotidine; tiotidine; TY-11345; Wy-45,727; and zaltidine.

15. Method as claimed in claim 14, wherein:

the nitroimidazoles are selected from the group consisting of metronidazole, apronidazole, azomycine, benzonidazole, carnidazole, demetridazole, etanidazole, flunidazole, misonidazole, nimorazole, ornidazole, panidazole, ronidazole, and tinidazole;

the macrolides are selected from the group consisting of azithromycine, clarithromycine and erythromycine; and the compounds of the family of tetracyclines are selected from the group consisting of tetracycline, chlortetracycline, doxycycline, glycocycline, guamecycline, lymecycline, methacycline and sancycline.

16. Method as claimed in claim 15, wherein:

the salt of bismuth is bismuth subcitrate;

the first antibiotic is metronidazole;

the second antibiotic is tetracycline; and the $K^+/Na^+$ATPase inhibitor or anti-$H_2$ is omeprazole.

17. Method as claimed in claim 1, wherein both internal and external capsules are stable at a temperature comprised between 5 and 50° C. and at a humidity comprised between 35 and 65%.

18. Method as claimed in claim 1, wherein both internal and external capsules are made of hard gelatin.

19. Method as claimed in claim 1, wherein the internal capsule has a format between 2 or 3 and the external capsule has a format between 0+ or 1.

20. Method as claimed in claim 19, wherein the external capsule has a format of 0+ and the internal one has a format 3.

21. Pharmaceutical dosage form for the oral administration of active principles in a triple therapy against the microorganisms *Helicobacter pylori*, the pharmaceutical dosage form comprising an internal capsule placed inside an external capsule, wherein the external capsule comprises a soluble salt of bismuth and a first antibiotic, and the internal capsule comprises a second antibiotic.

22. Pharmaceutical dosage form as claimed in claim 21, wherein the internal capsule further comprises a $K^+/Na^+$ATP-ase inhibitor or anti-$H_2$, whereby the pharmaceutical dosage form is for the oral administration of a quadruple therapy.

23. Pharmaceutical dosage form as claimed in claim 21, wherein the external capsule comprises a $K^+/Na^+$ATP-ase inhibitor or anti-$H_2$, whereby the pharmaceutical dosage form is for the oral administration of a quadruple therapy.

24. Pharmaceutical dosage form as claimed in claim 21, wherein:

the salt of bismuth is selected from the group consisting of bismuth subcitrate, bismuth aluminate, bismuth carbonate, bismuth citrate, colloidal bismuth subnitrate, bismuth germanate, bismuth germanium oxide, bismuth nitrate, bismuth oxide, bismuth oxychloride, bismuth phosphate, bismuth salicylate, bismuth subcarbonate, bismuth subnitrate, bismuth subsalicylate, bismuth tribromophenate, bismuth trioxyde, bismuth vanadate, and bismuth vanadium tetraoxide;

the first antibiotic is selected from the group consisting of the nitroimidazoles; and the second antibiotic is selected from the group consisting of the macrolides and the compounds of the family of tetracyclines.

25. Pharmaceutical dosage form as claimed in claim 24, wherein:

the nitroimidazoles are selected from the group consisting of metronidazole, apronidazole, azomycine, benzonidazole, carnidazole, demetridazole, etanidazole, flunidazole, misonidazole, nimorazole, ornidazole, panidazole, ronidazole, and tinidazole;

the macrolides are selected from the group consisting of azithromycine, clarithromycine and erythromycine; and the compounds of the family of tetracyclines are selected from the group consisting of tetracycline, chlortetracycline, doxycycline, glycocycline, guamecycline, lymecycline, methacycline and sancycline.

26. Pharmaceutical dosage form as claimed in claim 25, wherein:

the salt of bismuth is bismuth subcitrate;

the first antibiotic is metronidazole; and the second antibiotic is tetracycline.

27. Pharmaceutical dosage form as claimed in claim 22, wherein:

the salt of bismuth is selected from the group consisting of bismuth subcitrate, bismuth aluminate, bismuth carbonate, bismuth citrate, colloidal bismuth subnitrate, bismuth germanate, bismuth germanium oxide, bismuth nitrate, bismuth oxide, bismuth oxychloride, bismuth phosphate, bismuth salicylate, bismuth subcarbonate, bismuth subnitrate, bismuth subsalicylate, bismuth tribromophenate, bismuth trioxyde, bismuth vanadate, and bismuth vanadium tetraoxide;

the first antibiotic is selected from the group consisting of the nitroimidazoles;

the second antibiotic is selected from the group consisting of the macrolides and the compounds of the family of tetracyclines; and the $K^+/Na^+$ATPase inhibitor or anti-$H_2$ is selected from the group consisting of BY841; cimetidine; ebrotidine; etintidine; famotidine; flunarizine; ICI-162,846; lansoprazole; metiamide; mifentidine; niperotidine; nizatidine; omeprazole; oxmetidine; pantoprazole; rabeprazole; ramixotidine; ranitidine; ritanserin; roxatidine acetate hydrochloride; ZKF-93479; SKF-94482; sufotidine; tiotidine; TY-11345; Wy-45,727; and zaltidine.

28. Pharmaceutical dosage form as claimed in claim 27, wherein:

the nitroimidazoles are selected from the group consisting of metronidazole, apronidazole, azomycine, benzonidazole, carnidazole, demetridazole, etanidazole, flunidazole, misonidazole, nimorazole, ornidazole, panidazole, ronidazole, and tinidazole;

the macrolides are selected from the group consisting of azithromycine, clarithromycine and erythromycine; and the compounds of the family of tetracyclines are selected from the group consisting of tetracycline, chlortetracycline, doxycycline, glycocycline, guamecycline, lymecycline, methacycline and sancycline.

29. Pharmaceutical dosage form as claimed in claim 28, wherein:

the salt of bismuth is bismuth subcitrate;

the first antibiotic is metronidazole;

the second antibiotic is tetracycline; and the $K^+/Na^+$ATPase inhibitor or anti-$H_2$ is omeprazole.

30. Pharmaceutical dosage form as claimed in claim 23, wherein:

the salt of bismuth is selected from the group consisting of bismuth subcitrate, bismuth aluminate, bismuth carbonate, bismuth citrate, colloidal bismuth subnitrate, bismuth germanate, bismuth germanium oxide, bismuth nitrate, bismuth oxide, bismuth oxychloride, bismuth phosphate, bismuth salicylate, bismuth subcarbonate, bismuth subnitrate, bismuth subsalicylate, bismuth tribromophenate, bismuth trioxyde, bismuth vanadate, and bismuth vanadium tetraoxide;

the first antibiotic is selected from the group consisting of the nitroimidazoles;

the second antibiotic is selected from the group consisting of the macrolides and the compounds of the family of tetracyclines; and the $K^+/Na^+$ATPase inhibitor or anti-$H_2$ is selected from the group consisting of BY841; cimetidine; ebrotidine; etintidine; famotidine; flunarizine; ICI-162,846; lansoprazole; metiamide; mifentidine; niperotidine; nizatidine; omeprazole; oxmetidine; pantoprazole; rabeprazole; ramixotidine; ranitidine; ritanserin; roxatidine acetate hydrochloride; ZKF-93479; SKF-94482; sufotidine; tiotidine; TY-11345; Wy-45,727; and zaltidine.

31. Pharmaceutical dosage form as claimed in claim 30, wherein:

the nitroimidazoles are selected from the group consisting of metronidazole, apronidazole, azomycine, benzonidazole, carnidazole, demetridazole, etanidazole, flunidazole, misonidazole, nimorazole, ornidazole, panidazole, ronidazole, and tinidazole;

the macrolides are selected from the group consisting of azithromycine, clarithromycine and erythromycine; and the compounds of the family of tetracyclines are selected from the group consisting of tetracycline, chlortetracycline, doxycycline, glycocycline, guamecycline, lymecycline, methacycline and sancycline.

32. Pharmaceutical dosage form as claimed in claim 31, wherein:

the salt of bismuth is bismuth subcitrate;

the first antibiotic is metronidazole;

the second antibiotic is tetracycline; and the $K^+/Na^+$ATPase inhibitor or anti-$H_2$ is omeprazole.

33. Pharmaceutical dosage form as claimed in claim 21, wherein the internal capsule has a format between 2 or 3 and the external capsule has a format between 0+ or 1.

34. Pharmaceutical dosage form as claimed in claim 33, wherein the external capsule has a format of 0+ and the internal one has a format 3.

35. Pharmaceutical dosage form as claimed in claim 21, wherein the internal and external capsules are made of hard gelatin.

36. Pharmaceutical dosage form as claimed in claim 21, wherein the internal and external capsules contain respectively and independently one or more excipients.

37. Pharmaceutical dosage form as claimed in claim 17, wherein the excipients are selected from the group consisting of magnesium stearate; talc; cellulose and its derivates; silica and its derivates; sugars; polyethyglycols; wax, mono-, di- and tri-glycerids of hydrogenated fat acids; alcohols and acids at high molecular weight; and relevant mixtures thereof.

* * * * *